US011746390B2

(12) United States Patent
Huang et al.

(10) Patent No.: US 11,746,390 B2
(45) Date of Patent: Sep. 5, 2023

(54) METHOD FOR BREEDING SELF-COMPATIBLE POTATOES

(71) Applicants: Agricultural Genomics Institute, Chinese Academy of Agricultural Sciences, Shenzhen (CN); AGRICULTURAL GENOMICS INSTITUTE AT SHENZHEN, CHINESE ACADEMY OF AGRICULTURAL SCIENCES, Shenzhen (CN)

(72) Inventors: Sanwen Huang, Shenzhen (CN); Chunzhi Zhang, Shenzhen (CN); Zhongmin Yang, Shenzhen (CN); Die Tang, Shenzhen (CN)

(73) Assignees: Agricultural Genomics Institute, Chinese Academy of Agricultural Sciences, Shenzhen (CN); AGRICULTURAL GENOMICS INSTITUTE AT SHENZHEN, CHINESE ACADEMY OF AGRICULTURAL SCIENCES, Shenzhen (CN)

( * ) Notice: Subject to any disclaimer, the term of this patent is extended or adjusted under 35 U.S.C. 154(b) by 147 days.

(21) Appl. No.: 16/922,829

(22) Filed: Jul. 7, 2020

(65) Prior Publication Data
US 2020/0385819 A1 Dec. 10, 2020

Related U.S. Application Data

(63) Continuation-in-part of application No. PCT/CN2019/082197, filed on Apr. 11, 2019.

(30) Foreign Application Priority Data

Jun. 14, 2018 (CN) .......................... 201810611716.3
Jan. 24, 2019 (CN) .......................... 201910069945.1

(51) Int. Cl.
*C12Q 1/6895* (2018.01)
*A01H 1/02* (2006.01)
*A01H 6/82* (2018.01)
*A01H 1/04* (2006.01)

(52) U.S. Cl.
CPC ............. *C12Q 1/6895* (2013.01); *A01H 1/02* (2013.01); *A01H 1/022* (2021.01); *A01H 1/045* (2021.01); *A01H 6/827* (2018.05); *C12Q 2600/13* (2013.01); *C12Q 2600/158* (2013.01)

(58) Field of Classification Search
None
See application file for complete search history.

(56) References Cited

FOREIGN PATENT DOCUMENTS

| CN | 102770017 A | 11/2012 |
| CN | 105052724 A | 11/2015 |
| CN | 108849471 A | 11/2018 |
| CN | 109548646 A | 4/2019 |

OTHER PUBLICATIONS

Solanum tuberosum S-RNase 8, NCBI/GenBank accession No. MZ561411, published Aug. 7, 2021.*
Solanum tuberosum S-RNase 10, NCBI/GenBank accession No. MZ561413, published Aug. 7, 2021.*
Dzidzienyo et al., 2016, Allelic diversity of S-RNase alleles in diploid potato species, Theor. Appl. Genet. 129: 1985-2001.*
Keskin et al., 2004, A new, structurally nonredundant, diverse data set of protein-protein interfaces and its implications, Protein Science 13: 1043-1055.*
Guo et al., 2004, Protein tolerance to random amino acid change, Proceedings of the National Academy of Sciences USA 101: 9205-9210.*
Thornton et al., 2000, From structure to function: approaches and limitations, Nature Structural Biology, structural genomic supplement, Nov. 2000: 991-994.*
European Patent Office—Supplemental European Search Reportc, Application No. 19 819 225.4, Munich, Germany, Reference B35-2487-01 EP, Agricultural Genomics Institute, Chinese Academy of Agricultural Sciences, et al dated Mar. 5, 2021, date of completion of search Apr. 16, 2021.
Allelic Diversity of S-Rnase Alleles in Diploid Potato Species, Daniel K. Dzidzienyo, Glenn J. Bryan, Gail Wilde, Timothy P. Robbins, Theor Appl Genet (2016) 129:1895-2001, International Journal of Plant Breeding Research, vol. 129, No. 10, Aug. 6, 2016.
Genetics of Self-Compatibility in Dihaploids of Solanum Tuberosum L. I. Breeding Behaviour of Two Self-Compatible Dihaploids, Janny Olsder and J.G. TH. Hermsen, Intitute of Plant Breeding (IvP), Agricultural University, Wageningen, the Neterlands, Received Apr. 12, 1976, Euphytica 25 (1976) 597-607, vol. 25, No. 3, Jan. 1, 1976.

(Continued)

*Primary Examiner* — Brent T Page
(74) *Attorney, Agent, or Firm* — Flener IP & Business Law; Zareefa B. Flener

(57) ABSTRACT

Disclosed is a method for breeding self-compatible potatoes, including the following steps: (1) selecting a self-compatible potato variety material and referring to it as PG6359, and cloning the S-RNase gene of PG6359 through the transcriptome sequencing method; and (2) obtaining two full-length sequences of the S-RNase gene from the cloned S-RNase gene in step (1) and referring to them as $S_{s11}$ and $S_{s12}$ respectively, and after carrying out an artificial self-pollination for the variety material PG6359, selecting the variety material having the genotype of $S_{s11}S_{s11}$ from the offspring as the female parent, and selecting a self-incompatible material as the male parent, and then obtaining a self-compatible $F_1$ generation by hybridization. The invention overcomes the self-incompatibility of diploid potatoes, and does not require the introduction of any wild potato gene fragments, thereby avoiding linkage drag, and providing a basis for the rapid creation of a diploid potato inbred line.

7 Claims, No Drawings
Specification includes a Sequence Listing.

(56) References Cited

OTHER PUBLICATIONS

Breaking Self-Incompatibility in Diploid Potato Using the CRISPR/CAS9 System, Felix E. Enciso, Daniel Zarka, Satya Swathi Nadakuduti, C. Robin Buell, David Douches, Plant and Animal Genome XXVI conference (Jan. 1, 2018), The Largest Ag-Genomics Meeting in the World Jan. 13-17, 2018 San Diego, CA.
Sequence Listing for Solanum stenotomum self-incompatibility associated protein (S-RNase) mRNA, S-RNase-Ss9 allele, partial cds, GenBank: KX641188.1, submitted Aug. 1, 2016.
Sequence Listing for Solanum stenotomum self-incompatibility associated protein (S-RNase) mRNA, S-RNase-Ss1 allele, partial cds, GenBank: KX641180.1, submitted Aug. 1, 2016.
The Genetic Basis of Inbreeding Depression in Potato, Authors: Chunzhi Zhang, et al., Title of Item: Nature Genetics, Date: 2019-March, Relevant Pages of the Publication: 374-378, vol. Issue #: vol. 51(3), Publisher: Nature Publishing Group, Place of Publication: United Kingdom.
Genetics of Self-Compatibility in a Self-Incompatible Wild Diploid Potato Species Solanum Chacoense. 2. Localization Ofan S Locus Inhibitor (Sli) Gene on the Potato Genome Using DNA Markers, Authors: Kazuyoshi Hosaka, Robed E. Hanneman Jr., Title of Item: Euphytica, Date: Apr. 23, 1998, Relevant Pages of the Publication: 365-371, vol. Issue #: vol. 103, Publisher: Kluwer Academic Publishers, Place of Publication: Netherlands.
Generation of Self-Compatible Diploid Potato by Knockout of S-RNase, Authors: Mingwang Ye, et al., Title of Item: Nature Plants, Date: Aug. 13, 2008, Relevant Pages of the Publication: 651-654, vol. Issue #: vol. 4, Publisher: Nature Publishing Group, Place of Publication: United Kingdom.
Genome Sequence of M6, A Diploid Inbred Clone of the High-Glycoalkaloid-Producing Tuber-Bearing Potato Species Solanum Chacoense, Reveals Residual Heterozygosity, Authors: Couriney P. Leisner, et al., Title of Item: The Plant Journal, Date: Feb. 05, 2018, Relevant Pages of the Publication: 562-570, vol. Issue #: vol. 94, Publisher Blackwell Publishing Inc., Place of Publication: United Kingdom.
Reinvating Potato as a Diploid Inbred Line- Based Crop, Authors: Shelley H. Jansky, et al., Title of Item: Crop Science, Date: Jun. 24, 2016, Relevant Pages of the Publication: 1412-1422, vol. Issue #: vol. 56, Publisher: Crop Science Society of America, Place of Publication: United States.
Genetic Mapping with an Inbred Line-Derived F2 Population in Potato, Authors: Jeffrey B. Endelman, Shelley H. Jansky, Title of Item: Theoretical and Applied Genetics, Date: Feb. 05, 2016, Relevant Pages of the Publication 335-943, vol. Issue #: vol. 129, Publisher: Springer, Place of Publication: Germany.
M6: A Diploid Potato Inbred Line for Use in Breeding and Genetics Research, Authors: S.H. Jansky, et al., Title of tern: Journal of Plant Registrations, Date: Feb. 21, 2014, Relevant Pages of the Publication: 195-199, vol. Issue #: vol. 8, Publisher: Crop Science Society of America, Place of Publication: United States.
Nsertion Mutagenesis Using Tnt1 Retrotransposon in Potato, Authors: Saowapa Duangpan, et al., Title of Item: Plant Physiology, Date: 2013-September, Relevant Pages of the Publication: 21-29, vol. Issue #: vol. 163, Publisher: American Society of Plant Biologists, Place of Publication: United States.
Towards F1 Hybrid Seed Potato Breeding, Authors: Pim Lindhout, et al., Title of Item: Potato Research, Date: Dec. 15, 2011, Relevant Pages of the Publication: 301-312, vol. Issue #: vol. 54, Publisher: The Authors.
Toward the Developent of Highly Homozygous Diploid Potato Lines Using the Self-Compatibility Controlling SLI Gene, Authors: Chalermpol Phumichai, et al., Title of Item: Genome, Date: 2005-Nov. 29, Relevant Pages of the Publication: 977-984, vol. Issue #: vol. 48, Publisher: NRC Canada, Place of Publication: Canada.
Allelic Diversity of S-RNase Alleles in Diploid Potato Species, Authors: Daniel K. Dzidzienyo, et al., Title of Item Theoretical and Applied Genetics, Date:Aug. 06, 2016, Relevant Pages of the Publication: 1985-2001, vol. Issue #: vol. 129, Publisher: Springer, Place of Publication: Germany.
International Search Report, PCT/CN2019/082197, dated Jun. 14, 2019.

\* cited by examiner

US 11,746,390 B2

METHOD FOR BREEDING SELF-COMPATIBLE POTATOES

CROSS-REFERENCE TO RELATED APPLICATIONS

The present application is a continuation in part of International Application No PCT/CN2019/082197 (filed on Apr. 11, 2019), which claims the benefit and priority of Chinese patent application No. CN201810611716.3 (filed on Jun. 14, 2018) and application No. CN201910069945.1 (filed on Jan. 24, 2019), each of which is incorporated herein by reference in its entirety and for all purposes.

TECHNICAL FIELD

The invention relates to the technical field of genetic breeding, in particular to a method for breeding self-compatible potatoes.

BACKGROUND

Potatoes have comprehensive nutrition, the potato crop is the most important tuber food crop in the world, and it plays an important role in solving the global food crisis. However, two structural obstacles have been restricting the sustainable development of the potato industry: 1) cultivated potatoes are mainly autotetraploids, and the genetic analysis is very complicated, leading to long breeding cycles; 2) the asexuality reproduction of tetraploid potatoes by using potato blocks has the disadvantages of low reproduction coefficient (1:10), high cost of germplasm resource, and being easy to carry pests and diseases. In this case, scientists from different countries have called for further domestication of potatoes at the diploid level to change them into seed propagation crops. The genetics of diploid potatoes is simpler than that of tetraploid potatoes, and the coefficient of seed propagation is higher (1:5000), the seeds are convenient for storage and transportation and substantially do not carry diseases and pests. In fact, diploid potatoes exist extensively in nature. The latest taxonomic research has divided potatoes into 4 cultivars and 107 wild varieties, 70% of them are diploid potatoes. Fully exploiting the genetic variation in these diploid resources will greatly promote the genetic improvement of potatoes.

However, most of the diploid potatoes are self-incompatible, this severely limits the selection of inbred lines. Self-incompatibility of diploid potatoes belongs to gametophytic self-incompatibility, and is controlled by a high polymorphic S site. For a long time, researchers have been looking for self-compatible diploid potatoes. In 1998, Japanese researcher Hosaka reported a self-compatible wild potato line, Solanum chacoense chc525-3, which contains a Sli gene (S-locus inhibitor) inhibiting the self-incompatibility and leading to self-compatibility. However, the Sli gene is derived from wild potatoes, and the introduction of Sli gene into cultivars often results in many undesirable traits, such as the long length of stolons (greater than 1 meter), and high content of the toxic substance solanine, etc. Moreover, these undesirable traits are controlled by multiple genes, and it is difficult to eliminate them in practical breeding work. Therefore, the problem to be solved in the art is how to overcome the problem of self-incompatibility of diploid potatoes.

SUMMARY

In order to solve the technical problem of self-incompatibility of diploid potatoes, the present invention provides a method for breeding self-compatible potatoes, the method includes the following steps:

(1) selecting a self-compatible potato variety material and referring to it as PG6359, and cloning the S-RNase gene of PG6359 through the transcriptome sequencing method;

(2) obtaining two full-length sequences of the S-RNase gene from the cloned S-RNase gene in step (1) and referring to them as $S_{s11}$ and $S_{s12}$ respectively, wherein the gene sequence of $S_{s11}$ is represented by SEQ ID NO:1, and the gene sequence of $S_{s12}$ is represented by SEQ ID NO:2; and after carrying out an artificial self-pollination for the variety material PG6359, selecting the variety material having the genotype of $S_{s11} S_{s11}$ from the offspring as the female parent and referring to it as material A, and selecting a self-incompatible material as the male parent and referring to it as material B, then obtaining a self-compatible $F_1$ generation by hybridization; performing genotype detection for the $F_1$ generation to confirm that the $F_1$ generation contains the $S_{s11}$ gene, and detecting that the $F_1$ individuals are self-compatible after self-pollination of the $F_1$ generation.

The diploid potato resources are screened by artificial self-pollination at the flowering stage, and the self-compatible variety material PG6359 is finally obtained. Since the self-incompatibility is controlled by S-RNase gene at the S site, we firstly test whether the S-RNase gene of PG6359 is mutated. Among different potato variety materials, the polymorphism of S-RNase gene is very high, and the similarity of amino acids is 32.9%-94.5%. It is difficult to obtain the full-length sequence of S-RNase gene by homologous cloning method. Moreover, the S-RNase gene is specifically and highly expressed in style, so we successfully clone the S-RNase gene in PG6359 by transcriptome sequencing. The S-RNase gene at the S site refers to a nuclease specifically expressed in the stigma, and the nuclease can degrade ribosomal RNA in pollen tubes of the same S genotype, thereby inhibiting the extension of the pollen tubes in stigma and causing self-incompatibility.

Further, the transcriptome sequencing method in step (1) comprises: firstly extracting RNA by utilizing the style of PG6359, and performing the transcriptome sequencing by Illumina HiSeq® X Ten platform to obtain 2 Gb of sequencing data; de novo assembling the transcriptome data by Trinity software, and calculating the expression of each transcript by RSEM software; then performing BLAST® by utilizing the known S-RNase protein sequence in the potato reference genome, and selecting the sequence with an alignment reliability E value less than 1E-5 and an expression level FPKM value greater than 200 as a candidate sequence of the S-RNase gene; finally based on the alignment results, designing amplification primers to amplify the full length of the S-RNase gene of PG6359, and determining its expression by qPCR.

Further, in step (2), the $F_1$ single plant is used as a female parent, and the self-incompatible material B is used as a male parent to perform crossing and obtain a self-compatible $F_1$ generation.

A total of two S-RNase full-length sequences of PG6359 are obtained by using the method according to the present invention. Based on RSEM calculations, the expression level of $S_{s11}$ is 59.42, and the expression level of $S_{s12}$ is 5124.98; there is a differential of 100 times. With verification by qPCR, the expression level of $S_{s12}$ is 400 times as much as that of $S_{s11}$. Since S-RNase gene has nuclease activity, and it can degrade ribosomal RNA in pollen of the same S genotype, thereby inhibiting the extension of the pollen tube. The expression level of $S_{s11}$ found in the present invention is relatively low, and it may not be able to exert the effect of inhibiting the extension of the pollen tube. Furthermore, we carry out artificial self-pollination for PG6359, and obtain a large number of selfing offspring. Finally it is found that, the genotypes of the selfing offspring single plants are $S_{s11}S_{s12}$ and $S_{s11}S_{s11}$, but no $S_{s12}S_{s12}$ genotype is found. This indicates that due to normal expression of the $S_{s12}$ gene in the stigma, the pollen tube containing $S_{s12}$ is inhibited from extending, and the low-expressing $S_{s11}$ gene cannot reject the pollen containing the $S_{s11}$ genotype, thereby resulting in self-compatibility. The $S_{s11}$ gene of PG6359 can be introduced into other self-incompatible materials by hybridization, and the self-incompatible materials can be changed into self-compatible materials.

Further, the sequence of the upstream primer of the amplification primers is represented by SEQ ID NO:3, and the sequence of the downstream primer of the amplification primers is represented by SEQ ID NO:4.

Another aspect of the present invention provides a polynucleotide comprising or consisting of the following sequence:

(1) the nucleotide sequence represented by SEQ ID NO:1; or (2) the complementary sequence, degenerate sequence, or homologous sequence of SEQ ID NO:1, wherein the homologous sequence is a polynucleotide having about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity to the nucleotide represented by SEQ ID NO:1; or (3) a polynucleotide hybridizing to a nucleotide sequence of SEQ ID NO: 1 under stringent conditions and encoding a protein having S-RNase enzyme activity, or a complementary sequence thereof.

Another aspect of the present invention provides a potato plant, and a plant part, a tuber, a tuber part, a seed, or a plant cell thereof, wherein it comprises the above polynucleotide.

In a specific embodiment of the present invention, the potato plant, the plant part, tuber, tuber part, seed, or the plant cell thereof is a self-compatible material.

In a specific embodiment of the present invention, the expression level of the S-RNase gene in the potato plant, and the plant part, tuber, tuber part, seed, or the plant cell thereof is less than 100 by RSEM calculation; preferably, the expression level of the S-RNase gene is less than 60, and more preferably, the expression level of the S-RNase gene is close to zero.

In a specific embodiment of the present invention, a nucleotide sequence of the S-RNase allele represented by SEQ ID NO:1 ($S_{s11}$), or a complementary sequence, degenerate sequence, homologous sequence thereof is expressed.

In a specific embodiment of the present invention, another nucleotide sequence of the S-RNase allele represented by SEQ ID NO:1 ($S_{s11}$) or a complementary sequence, degenerate sequence, homologous sequence thereof, or represented by SEQ ID NO:2 ($S_{s12}$) or a complementary sequence, degenerate sequence, homologous sequence thereof is expressed.

In a specific embodiment of the present invention, the homologous sequence may be a polynucleotide obtained by hybridizing to a nucleotide sequence in SEQ ID NO: 1 or SEQ ID NO: 2 or a complementary sequence thereof under stringent conditions, or a fragment thereof;

The "stringent conditions" described herein may be any of a low stringent condition, a medium stringent condition, and a high stringent condition; and preferably a high stringent condition. Exemplarily, the "low stringent conditions" may be conditions of 30° C., 5×SSC, 5×Denhardts solution, 0.5% SDS, 52% formamide; the "medium stringent conditions" may be conditions of 40° C., 5×SSC, 5×Denhardts solution, 0.5% SDS, 52% formamide; and the "high stringency conditions" may be conditions of 50° C., 5×SSC, 5×Denhardts solution, 0.5% SDS, 52% formamide. Those skilled in the art will understand that the higher the temperature, the more homologous polynucleotides may be obtained. In addition, a person skilled in the art may select a comprehensive result produced by a plurality of factors such as temperature, probe concentration, probe length, ionic strength, time, and salt concentration that affect the rigor of the hybridization, so as to achieve the corresponding rigor.

In addition, the hybridizable polynucleotide also may be such a homologous polynucleotide, when calculated by using homology search softwares such as FASTA and BLAST® and the default parameters set by the system, it has about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity to a polynucleotide encoding the phosphoglycerate kinase of the present invention.

The nucleotide sequence homology may be determined by using Karlin and Altschul's algorithm rules BLAST® (Proc. Natl. Acad. Sci. USA 87: 2264-2268, 1990; Proc. Natl. Acad. Sci. USA 90: 5873, 1993). Programs BLASTN and BLASTX based on the rules of the BLAST® algorithm have been developed (Altschul S F, et al: J Mol Mol Biol 215: 403, 1990). When BLASTN is used to analyze the base sequence, for example, the parameters are: score=100, and wordlength=12; when BLAST® and Gapped BLAST® programs are used, the default parameter values may be set for using the system of each program.

Another aspect of the present invention provides a method for generating self-compatible potatoes, which comprises performing selfing by using a potato plant comprising the above polynucleotide, or the above potato plant, or a potato plant produced by a plant part, a tuber, a tuber part, a seed or a plant cell thereof as parent.

Another aspect of the present invention provides a method for generating self-compatible potatoes, which comprises performing hybridization by using a potato plant comprising the above polynucleotide, or a potato plant produced by a plant part, a tuber, a tuber part, a seed or a plant cell thereof as the first parent A, so that the offspring comprises the above polynucleotide.

In a specific embodiment of the present invention, hybridization is performed by using a potato plant comprising the above polynucleotide as the first parent A, and a self-incompatible material B as a second parent.

In a specific embodiment of the present invention, backcross is performed by using offspring comprising the above polynucleotide as the first parent, and a self-incompatible material B as a second parent, so as to obtain a self-compatible material with a genetic background of the material B.

For example, $F_1$ is used as the female parent, and self-incompatible material B is used as the male parent for backcrossing to obtain the $FB_1$ generation plants. With genotype detection, an individual $F_2$ containing the $S_{s11}$ gene is obtained; further, $F_2$ is used as the female parent, and self-incompatibility material B is used as the male parent to perform backcross; after multiple generations of backcrossing, then performing another generation of self-crossing, a new self-incompatible material with a genetic background of the material B may be obtained.

In a specific embodiment of the present invention, the S-RNase genotype of the female parent contains $S_{s11}$, and preferably, the S-RNase genotype of the female parent is $S_{s11}S_{s11}$.

Another aspect of the present invention provides a potato plant, or a plant part, tuber, tuber part, and seed thereof produced by the above breeding method.

Another aspect of the present invention provides a method for manufacturing a commercial plant product, which comprises: obtaining the above potato plant, and a plant part, a tuber, a tuber part, a seed or a plant cell thereof to manufacture the commercial plant products, wherein the plant products are selected from the group consisting of: fresh whole potatoes, French fries, potato chips, dehydrated potato materials, potato flakes, and potato granules.

Another aspect of the present invention provides a food made from a potato plant, a tuber or a tuber part which is produced by growing of the above potato plant, and a plant part, a tuber, a tuber part, or a plant cell or a seed thereof.

In a specific embodiment of the present invention, the food is a sliced potato tuber food.

In a specific embodiment of the present invention, the food is a group consisting of French fries, potato chips, and baked potatoes.

The invention adopting the above technical solutions has the following beneficial effects: it enables to overcome the self-incompatibility of diploid potatoes, and the present invention does not require the introduction of any wild potato gene fragments, thereby avoiding linkage drag, and providing a basis for the rapid creation of a diploid potato inbred line.

DETAILED DESCRIPTION OF EMBODIMENTS

Explanation:

The highly polymorphic S-site described herein is the S-RNase protein, which has multiple morphologies, for example, $S_{s11}$ and $S_{s12}$ are two different morphologies with different amino acid sequences. The S-RNase described herein may represent both the S-RNase protein and the gene determining the expression of the S-RNase protein, and the specific reference may be inferred from the contextual understanding. Similarly, $S_{s11}$ and $S_{s12}$ may either respectively represent a variant form of the S-RNase protein, or respectively represent the gene determining the variant form, and the specific reference may be inferred from the contextual understanding.

The expression level of the S-RNase gene described herein refers to the content of mRNA transcribed by S-RNase gene.

Example 1: A method for breeding self-compatible potatoes disclosed in the present invention includes the following steps:

(1) performing artificial self-pollination for more than 200 diploid potatoes at flowering stage, selecting a self-compatible potato variety material and referring to it as PG6359, and cloning the S-RNase gene of PG6359 through the transcriptome sequencing method;

(2) obtaining two full-length sequences of the S-RNase gene from the cloned S-RNase gene in step (1) and referring to them as $S_{s11}$ and $S_{s12}$ respectively, wherein the gene sequence of $S_{s11}$ is represented by SEQ ID NO:1, and the gene sequence of $S_{s12}$ is represented by SEQ ID NO:2; and after carrying out an artificial self-pollination for the variety material PG6359, selecting the variety material having the genotype of $S_{s11}S_{s11}$ from the offspring as the female parent and referring to it as material A, and selecting a self-incompatible material as the male parent and referring to it as material B, then obtaining a self-compatible $F_1$ generation by hybridization; performing genotype detection for the $F_1$ generation to confirm that the $F_1$ generation contains the $S_{ss1}$ gene, and determining that all the $F_1$ individuals are self-compatible after self-pollination of the $F_1$ generation.

Two full-length S-RNase sequences of PG6359 are obtained. Based on RSEM calculations, the expression level of $S_{s11}$ is 59.42, and the expression level of $S_{s12}$ is 5124.98; there is a differential of 100 times. With verification by qPCR, the expression level of $S_{s12}$ is 400 times as much as that of $S_{s11}$. Since S-RNase gene has nuclease activity, and it can degrade ribosomal RNA in pollen of the same S genotype, thereby inhibiting the extension of the pollen tube. The expression level of $S_{s11}$ found in the present invention is relatively low, and it may not be able to exert the effect of inhibiting the extension of the pollen tube. In order to verify this hypothesis, we carry out artificial self-pollination for PG6359, and obtain a large number of selfing offspring. After detection of the S genotypes for 201 offspring, it is found that the genotypes of 105 single plants are $S_{s11}S_{s12}$, and the genotypes of 96 single plants are $S_{s11}S_{s11}$, but no $S_{s12}S_{s12}$ genotype is found. This indicates that due to normal expression of the $S_{s12}$ gene in the stigma, the pollen tube containing $S_{s12}$ is inhibited from extending, and the low-expressing $S_{s11}$ gene cannot reject the pollen containing the $S_{s11}$ genotype, thereby resulting in self-compatibility. Since all the offspring of PG6359 contain the lower expression $S_{s11}$ gene, they should theoretically be self-compatible. After performing self-pollination for the offspring, it is found that except for several materials without blooming or having poor pollen vitality, the other materials are self-compatible.

The operation methods without specific illustration in this Example all belong to the prior art, so they are not explained too much here.

Example 2: A method for breeding self-compatible potatoes disclosed in the present invention includes the following steps:

(1) selecting a self-compatible potato variety material and referring to it as PG6359, and cloning the S-RNase gene of PG6359 through the transcriptome sequencing method;

(2) obtaining two full-length sequences of the S-RNase gene from the cloned S-RNase gene in step (1) and referring to them as $S_{s11}$ and $S_{s12}$ respectively, wherein the gene sequence of $S_{s11}$ is represented by SEQ ID NO:1, and the gene sequence of $S_{s12}$ is represented by SEQ ID NO:2; and after carrying out an artificial self-pollination for the variety material PG6359, selecting the variety material having the genotype of $S_{s11}S_{s11}$ from the offspring as the female parent and referring to it as material A, and selecting a self-incompatible material as the male parent and referring to it as material B, then obtaining a self-compatible $F_1$ generation by hybridization; performing genotype detection for the $F_1$ generation to confirm that the $F_1$ generation contains the $S_{ss1}$ gene, and detecting that the $F_1$ individuals are self-compatible after self-pollination of the $F_1$ generation.

Particularly, the transcriptome sequencing method in step (1) comprises: firstly extracting RNA by utilizing the style of PG6359, and performing the transcriptome sequencing by Illumina HiSeq® X Ten platform to obtain 2 Gb of sequencing data; de novo assembling the transcriptome data by Trinity software, and calculating the expression of each transcript by RSEM software; then performing BLAST® by utilizing the known S-RNase protein sequence in the potato reference genome, and obtaining a candidate sequence of the S-RNase allele in the transcriptome data; finally based on the alignment results, designing amplification primers to amplify the full length of the S-RNase gene of PG6359, and determining its expression by qPCR.

Further in step (2), the $F_1$ single plant is used as a female parent, and the self-incompatible material B is used as a male parent to perform backcrossing; then performing genotype detection for the resulting $BC_1$ generation material to obtain the individual containing $S_{s11}$ gene as the female parent, and continuing to backcross with the self-incompatible material B; after multiple generations of backcrossing, then performing another generation of self-crossing, a new self-compatible material with a genetic background of the material B may be obtained.

Two full-length S-RNase sequences of PG6359 are obtained in the invention. Based on RSEM calculations, the expression level of $S_{s11}$ is 58.42, and the expression level of $S_{s12}$ is 5814.98; there is a differential of 100 times. With verification by qPCR, the expression level of $S_{s12}$ is 400 times as much as that of $S_{s11}$. It should be explained here that the expression data of $S_{s11}$ and $S_{s12}$ are obtained from multiple times of parallel experiments. With RSEM calculation and qPCR verification, it can be accurately determined that the expression level of $S_{s11}$ is indeed low, and the low-expressing $S_{s11}$ gene cannot reject the pollen containing the $S_{s11}$ genotype, thereby resulting in self-compatibility.

Further, the sequence of the upstream primer of the amplification primers is represented by SEQ ID NO:3, and the sequence of the downstream primer of the amplification primers is represented by SEQ ID NO:4. The selected amplification primers have strong specificity and can amplify the full-length sequence of S-RNase gene very well and completely.

The operation methods without specific illustration in this Example all belong to the prior art, so they are not explained too much here.

The above descriptions are merely preferred Examples of the present invention, and are not intended to limit the present invention. For those skilled in the art, the present invention may have various modifications and changes. Any modification, equivalent substitution, or improvement made within the spirit and principle of the present invention shall be encompassed in the protection scope of the present invention.

What is claimed is:

1. A method for breeding self-compatible potatoes, comprising the following steps:
(1) selecting a self-compatible potato variety material and referring to it as a variety material PG6359, and cloning the S-RNase gene of the variety material PG6359 through the transcriptome sequencing method; wherein the transcriptome sequencing method comprises: firstly extracting RNA by utilizing the variety material PG6359, and performing the transcriptome sequencing by the sequencing platform to obtain 2 Gb of sequencing data; de novo assembling the transcriptome data by Trinity software, and calculating the expression of each transcript by RNASeq by Expectation Maximization (RSEM) software; then performing the sequence alignment search tool by utilizing the known S-RNase protein sequence in the potato reference genome, and selecting the sequence with an alignment reliability E value less than 1E-5 and an expression level Fragments Per Kilobase of exon model per Million mapped fragments (FPKM) value greater than 200 as a candidate sequence of the S-RNase gene; designing amplification primers to amplify the full length sequence of the S-RNase gene of variety material PG6359, and determining its expression by qPCR; and (2) obtaining two full-length sequences of the S-RNase gene from the cloned S-RNase gene in step (1) and referring to them as $S_{s11}$ and $S_{s12}$ respectively, wherein the gene sequence of $S_{s11}$ is shown in SEQ ID NO:1, and the gene sequence of $S_{s12}$ is shown in SEQ ID NO:2; and after carrying out an artificial self-pollination for the variety material PG6359, selecting the variety material having the genotype of $S_{s11} S_{s11}$ from the offspring as the female parent and referring to it as material A, and selecting a self-incompatible material as the male parent and referring to it as material B, then obtaining a self-compatible $F_1$ generation by hybridization; performing genotype detection for the $F_1$ generation to confirm that the $F_1$ generation contains the $S_{s11}$ gene, and detecting that individuals of the $F_1$ generation are self-compatible after self-pollination of the $F_1$ generation.

2. The method for breeding self-compatible potatoes according to claim 1, wherein the individual of the $F_1$ generation is used as a female parent in step (2), and the self-incompatible material B is used as a male parent to perform backcross; then performing genotype detection for the resulting $BC_1$ generation material to obtain the individual containing $S_{s11}$ gene as the female parent, and continuing to backcross with the self-incompatible material B; after multiple generations of backcrossing, then performing another generation of self-crossing.

3. The method for breeding self-compatible potatoes according to claim 1, wherein the sequence of the upstream primer of the amplification primers is shown in SEQ ID NO:3, and the sequence of the downstream primer of the amplification primers is shown in SEQ ID NO:4.

4. A method for generating self-compatible potatoes, comprising performing hybridization by using a potato plant comprising the polynucleotide shown in SEQ ID NO:1 as the first parent, so that the offspring comprises the polynucleotide, wherein the S-RNase genotype of the female parent is $S_{s11}S_{s11}$.

5. A method for generating self-compatible potatoes, comprising performing hybridization by using the potato plant, or a potato plant produced by a plant part, a tuber, a tuber part, a seed or a plant cell thereof comprising SEQ ID NO:1 as the first parent, so that the offspring comprises the polynucleotide, wherein the S-RNase genotype of the female parent is $S_{s11}S_{s11}$.

6. The method for generating self-compatible potatoes according to claim 5, wherein the second parent is a self-incompatible material.

7. The method according to claim 6, further performing backcross by using the offspring comprising the polynucleotide the first parent, and the self-incompatible material as the second parent, so as to obtain a self-compatible material having the genetic background of the second parent.

* * * * *

SEQUENCE LISTING

```
<160> NUMBER OF SEQ ID NOS: 4

<210> SEQ ID NO 1
<211> LENGTH: 645
<212> TYPE: DNA
<213> ORGANISM: Artificial Sequence
<220> FEATURE:
<223> OTHER INFORMATION: The gene sequence of Ss11 in S-RNase gene

<400> SEQUENCE: 1
atgtttagag ctcaccttac gttaggtttc ttcattctgc tttgtgtttt ttctcacgtt      60
catgggactt tgaccaatt gcaactggtt ttaagatggc ctacatcctt ttgcattggg     120
aaaaattgcg agagaactcc aaaaaacttt acaatccatg ggctttggcc ggatagcgtg     180
ggtggagaac tgaattactg tgatggcaaa gctaagtata ctagggtcaa ggatgaagca     240
tttgataaga ggaataagca ctggcctgac ttgttactaa gcgatgctga taatctgaaa     300
aaccaaggtt tctgggtaca tgaatacaga aagcatggat cgtgttgtaa aaatctcttc     360
aatgaaaaac aatactttga tttagcattg gttttaaaag acaggtttga tcttctgacg     420
actttcagaa atcacggaat tgttcctgaa tcatctcata ctgttcataa aattgaaaaa     480
actattaggt cagttactgg ggttcttcct aatctctctt gcactaaaaa tatggatctt     540
ttggagatag ggatatgttt caaccgagac gcaagtaata tgattgattg tccaaggcct     600
aagacgtgca gccctggcga aaataatctg attgcatttc catga                    645

<210> SEQ ID NO 2
<211> LENGTH: 645
<212> TYPE: DNA
<213> ORGANISM: Artificial Sequence
<220> FEATURE:
<223> OTHER INFORMATION: The gene sequence of Ss12 in S-RNase gene

<400> SEQUENCE: 2
```

-continued

```
atgtttaaac cacaagtcac atcagcactc ttcattgtac ttttctttc tcccacttat      60 gggaatttcg atcaattgca actggtattg acatggccag catcattttg ccacgccaat    120
aattgtaagc ggatagctcc aaaaaacttt acgattcacg ggctttggcc ggataaagag    180
ggaacactgc tgcagaactg caagccatta cctacgtata tacatttcgc ggataagatg    240
ctcaatgatc ttgacaaaaa ctggattcaa ttgaagtatc cagaacgttt tgctcgaaag    300
gaacaacctt tatggctata tcaatatcta aagcatggat cctgttgtca gaaagtttac    360
gatcaaaaca cgtattttag tctagctttg cgcttaaaag acaggtttga tcttctgaga    420
actctccaat tacatcgaat tgttcctgga tcaagttata catttaaaga aatctttgat    480
gccgtcaaga cagttagtca aacagatcct gacgtcaagt gtacaaaagg agcacaggaa    540
ctatatgaga taggcatatg tttcacccca aatgcagata gtctgattcc ttgtcgtcaa    600
agtgaaacat gtgacaaatc gaaagaaatc tttttcgta gatga                    645
```

<210> SEQ ID NO 3
<211> LENGTH: 23
<212> TYPE: DNA
<213> ORGANISM: Artificial Sequence
<220> FEATURE:
<223> OTHER INFORMATION: The upstream primer for amplifying the full
      length sequence of S-RNase gene of PG6359

<400> SEQUENCE: 3
cggaagaaag gaaatgaagt gag                                            23

<210> SEQ ID NO 4
<211> LENGTH: 20
<212> TYPE: DNA
<213> ORGANISM: Artificial Sequence
<220> FEATURE:
<223> OTHER INFORMATION: The downstream primer for amplifying the full
      length sequence of S-RNase gene of PG6359

<400> SEQUENCE: 4
aattacagca aggggagggg                                                20